(12) United States Patent
Percival et al.

(10) Patent No.: US 6,669,340 B2
(45) Date of Patent: Dec. 30, 2003

(54) ALIGNMENT SYSTEM FOR AN OPHTHALMIC INSTRUMENT

(75) Inventors: Christopher J. Percival, Williamsville, NY (US); Douglas H. Hoover, Corfu, NY (US)

(73) Assignee: Reichert, Inc., Depew, NY (US)

( * ) Notice: Subject to any disclaimer, the term of this patent is extended or adjusted under 35 U.S.C. 154(b) by 92 days.

(21) Appl. No.: 09/992,756

(22) Filed: Nov. 6, 2001

(65) Prior Publication Data
US 2003/0086059 A1 May 8, 2003

(51) Int. Cl.⁷ .................................................. A61B 3/14
(52) U.S. Cl. ........................................................ 351/208
(58) Field of Search .............................. 351/205, 206, 351/208, 221, 211

(56) References Cited

U.S. PATENT DOCUMENTS

| | | | |
|---|---|---|---|
| 3,585,849 A | 6/1971 | Grolman | 73/80 |
| 3,756,073 A | 9/1973 | Lavallee et al. | 73/80 |
| 4,665,923 A | 5/1987 | Kobayashi | 128/648 |
| 4,881,807 A | 11/1989 | Luce et al. | 351/208 |
| 4,995,393 A | * | 2/1991 | Katsuragi et al. | 351/208 |
| 6,042,544 A | 3/2000 | Miwa et al. | 600/399 |

FOREIGN PATENT DOCUMENTS

EP  1 121 895 A2  8/2001

\* cited by examiner

*Primary Examiner*—George Manuel
(74) *Attorney, Agent, or Firm*—Hodgson Russ LLP (57) ABSTRACT

An alignment system for an ophthalmic instrument comprises an optical axis along which an operator can directly view the patient's eye and the patient can fixate on a dark fixation target surrounded by a bright background that helps to illuminate the eye for operator viewing. A position detection system utilizing stored geometrical relationships determined by multiple regression during instrument calibration computes X-Y-Z alignment status of the instrument relative to a patient's eye based on local x-y position information from a pair of lateral detectors receiving corneally reflected light from a corresponding pair of lateral light sources. A heads-up display image is provided along an optical axis of the instrument for supplying instructive cues to an operator for moving the instrument to achieve alignment based on signal information from the position detection system, whereby the operator sees both a direct macro-image of the patient's eye and the display image. The alignment system is particularly suitable for use in hand-held ophthalmic instruments.

12 Claims, 7 Drawing Sheets

ALIGNMENT SYSTEM FOR AN OPHTHALMIC INSTRUMENT

BACKGROUND OF THE INVENTION

I. Field of the Invention

The present invention relates generally to alignment systems for enabling an operator to position an ophthalmic instrument relative to an eye of a patient, and more particularly to an alignment system that is well-suited for use in a hand-held ophthalmic instrument and that provides an operator with a direct view of a patient's eye as a positioning aid.

II. Description of the Related Art

Alignment systems for use by an operator in locating an ophthalmic instrument relative to an eye of a patient vary in complexity. In instruments where alignment is critical to measurement accuracy, for example in non-contact tonometers, it is commonplace to provide means for projecting a visible fixation target image along a measurement axis of the instrument to direct the patient's gaze, and to further provide an opto-electronic position detection system capable of sensing the position of the instrument relative to the eye. Where the ophthalmic instrument is a non-contact tonometer having a discharge tube for directing a fluid pulse at the eye, X-Y alignment is typically achieved by aligning an axis of the discharge tube to intersect with the corneal vertex, and Z alignment is achieved by positioning a fluid exit end of the discharge tube at a predetermined distance from the corneal vertex.

U.S. Pat. No. 3,756,073 to Lavallee et al. describes a non-contact tonometer having a target projecting system that projects an image of a target along an alignment axis through an objective lens to the image plane of the objective lens. Consequently, when the image plane of the objective lens is coincident with the center of curvature of the patient's cornea, a corneal virtual or mirror image of the target is re-imaged by the lens and a telescope lens in the plane of a circle reticle on the alignment axis. An operator looking through an eyepiece along the alignment axis toward the eye can see the retro-reflected target image superimposed on the circle reticle, and aligns the instrument laterally and vertically (X-Y alignment) by centering the target image with respect to the reticle markings. According to this system, the corneal surface under observation is limited to a desired small portion of the entire corneal surface. The '073 patent also describes a passive "go/no go" alignment confirmation system comprising an infra-red LED cooperating with an alignment detector located behind a pinhole aperture, whereby the detector generates a trigger signal upon alignment.

A more sophisticated opto-electronic alignment system for use in locating an ophthalmic instrument relative to an eye is taught in U.S. Pat. No. 4,881,807 to Luce et al. According to this system, and other systems of the prior art, triangulation is used to gauge the three-dimensional location of the eye relative to the instrument. By way of example, the aforementioned U.S. Pat. No. 4,881,807 discloses a system wherein two light sources arranged on opposite sides of the eye illuminate the eye with divergent rays, and a pair of CCD area detectors each comprising a two-dimensional array of light-sensitive pixels are arranged behind associated pinhole apertures to receive a small bundle of reflected rays originating from a corresponding one of the light sources. A local x-y location where the light strikes the CCD array is determined by identifying the pixel registering the peak response signal. The local x-y locations where light strikes each CCD array and specifications describing the predetermined geometric arrangement of the system components are provided as inputs to a microprocessor, which then calculates the amount of movement in the global X, Y, and Z directions necessary to achieve alignment. A video image detector is also provided to supply a macro-image of the eye to a CRT display, and output from the alignment CCD electronics is coupled into the CRT display electronics to provide alignment illumination spot symbols on the video display image.

Known alignment systems do not afford the operator a direct view of the eye along an alignment axis or main optical axis of the instrument for alignment purposes. In fact, many prior art systems rely on generating and displaying a video image of the eye and superimposing alignment cues in the displayed video image for moving the instrument to achieve alignment. This approach requires instrumentation that adds to the size, weight, and expense of the instrument.

BRIEF SUMMARY OF THE INVENTION

Therefore, it is an object of the present invention to provide an alignment system for an ophthalmic instrument that affords the operator a direct view of the patient's eye along an optical axis of the instrument.

It is another object of the present invention to provide an alignment system for an ophthalmic instrument that affords the operator a direct view of the patient's eye along an optical axis of the instrument while simultaneously presenting a fixation target to the patient along the optical axis.

It is another object of the present invention to provide an alignment system for an ophthalmic instrument that includes an instructive display image superimposed with the directly viewed real image of the eye in the operator's field of view.

It is yet another object of the present invention to provide an alignment system for an ophthalmic instrument that is relatively inexpensive to manufacture.

In furtherance of these and other objects, an ophthalmic instrument having a central optical axis to be aligned with a patient's corneal vertex comprises an eyepiece along the optical axis for enabling an operator to directly view the patient's eye for generalized alignment, and means for presenting a dark fixation target surrounded by a bright background to the patient along the same optical axis, wherein the bright background helps to illuminate the eye for operator viewing.

An alignment system according to a preferred embodiment further comprises an afocal position detection system for determining X-Y-Z alignment status of the instrument relative to the patient's eye. The position detection system comprises first and second light sources on opposite sides of the central optical axis of the instrument, and corresponding first and second light-sensitive area detectors positioned to receive light from an associated light source after it has been reflected by the cornea. The detectors provide signal information indicative of the local x-y position of an illumination spot formed thereon. In a preferred embodiment, the first and second detectors are quad-cell detectors having four quadrants, and the illumination spot size is about the size of one quadrant, whereby the x-y position can be determined based on the four signal levels generated by the quadrants. Collector lenses after each light source and in front of each detector minimize vergence in the light beam as it illuminates the eye and as it arrives at a detector.

The local x-y data from each detector are then provided as input to a series of stored geometrical relationships determined during instrument calibration for giving the X-Y-Z global alignment status of the instrument relative to the eye. The geometrical relationships are multiple regression equations for X, Y, and Z, wherein regression coefficients for each equation are determined by reading local x-y data from the detectors for an artificial eye placed at a plurality of known X-Y-Z positions during calibration. The regression coefficients are stored during calibration and used during normal instrument operation to quickly calculate X, Y and Z coordinates based on local x-y data from the detectors as an operator positions the instrument relative to a patient's eye.

A "heads-up" display is preferably connected to receive the X-Y-Z position data and provide instructional cues to the operator for moving the instrument to achieve alignment. In a current embodiment, the heads-up display comprises a polar array of light emitting diodes selectively illuminated to indicate a desired X-Y movement direction, and a linear array of light emitting diodes selectively illuminated to indicate a desired Z movement direction. An image of the heads-up display is presented to the operator along the instrument optical axis through the use of a beamsplitter that allows a macro-image of the patient's eye to be transmitted as well along the optical axis, whereby X-Y polar array is arranged circumferentially about the directly viewed macro-image of the eye.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
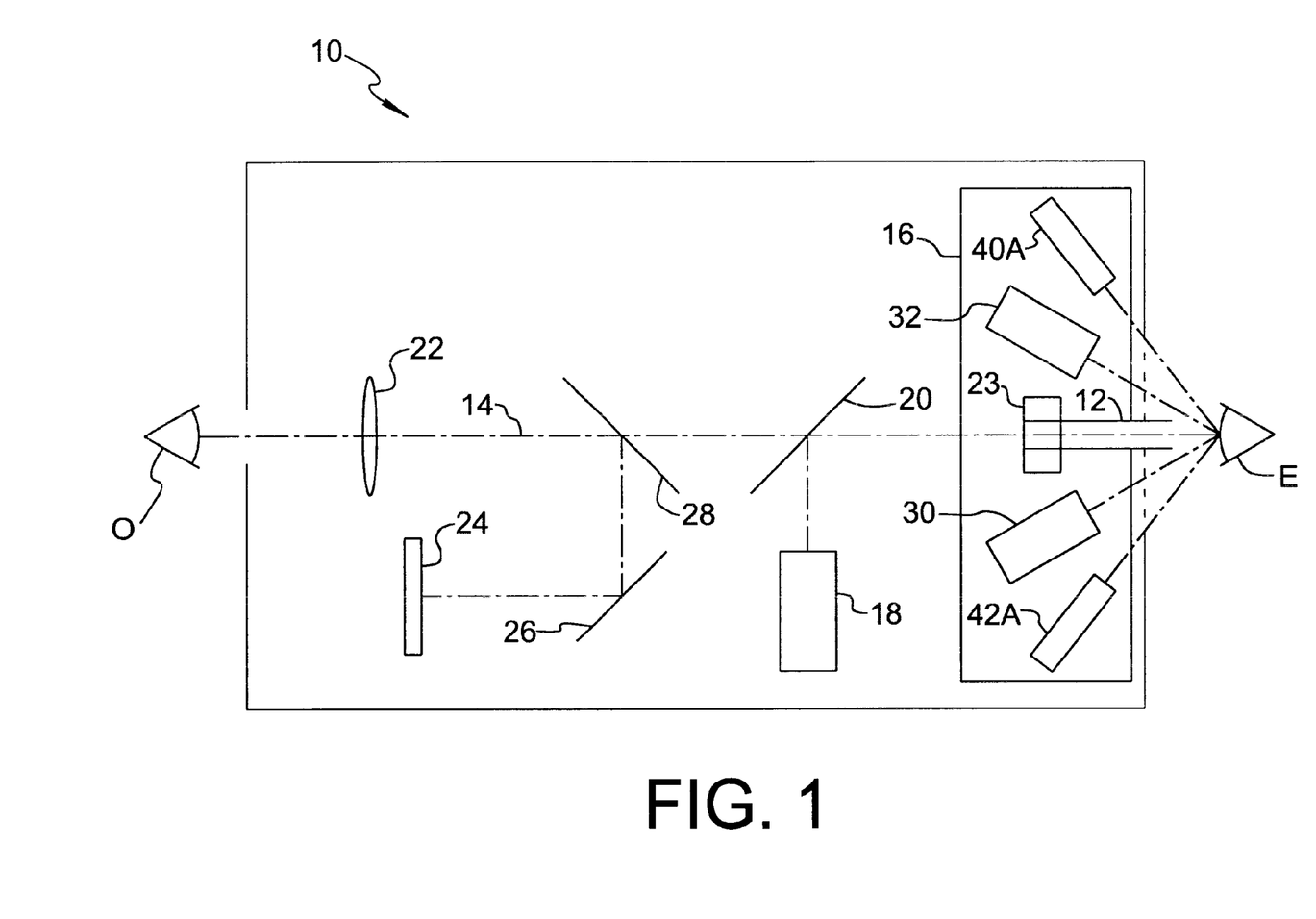
FIG. 1 is an optical schematic diagram of an ophthalmic instrument incorporating an alignment system of the present invention.

In FIG. 1, an ophthalmic instrument incorporating an alignment system of the present invention is illustrated schematically and identified by the reference numeral 10. Instrument 10 is depicted as being a non-contact tonometer operable to discharge a fluid pulse through a fluid discharge tube 12 to cause observable deformation of a patient's cornea for purposes of measuring intraocular pressure. However, the present invention may be implemented in other types of ophthalmic instruments where it is necessary to ascertain the X-Y or X-Y-Z alignment status of the instrument relative to an eye.

Instrument 10 includes an optical axis 14 along which discharge tube 12 is aligned, a nosepiece 16 fixed near a front portion of the instrument for mounting various optical and opto-electronic elements of the instrument as described below, a fixation target projecting system 18 cooperating with a beamsplitter 20 to present a visible fixation target to the patient along optical axis 14, an eyepiece 22 and a macro-lens 23 for enabling an operator O to view the patient's eye E through the instrument along optical axis 14, a heads-up display 24, and a mirror 26 cooperating with a beamsplitter 28 to present an image of the heads-up display to the operator along optical axis 14. Macro-lens 23 is preferably a planar—planar lens such that the operator sees the eye in an unmagnified state, however it is possible to use a macro-lens having optical power to provide some other desired field of view with respect to the eye.

Figure 2:
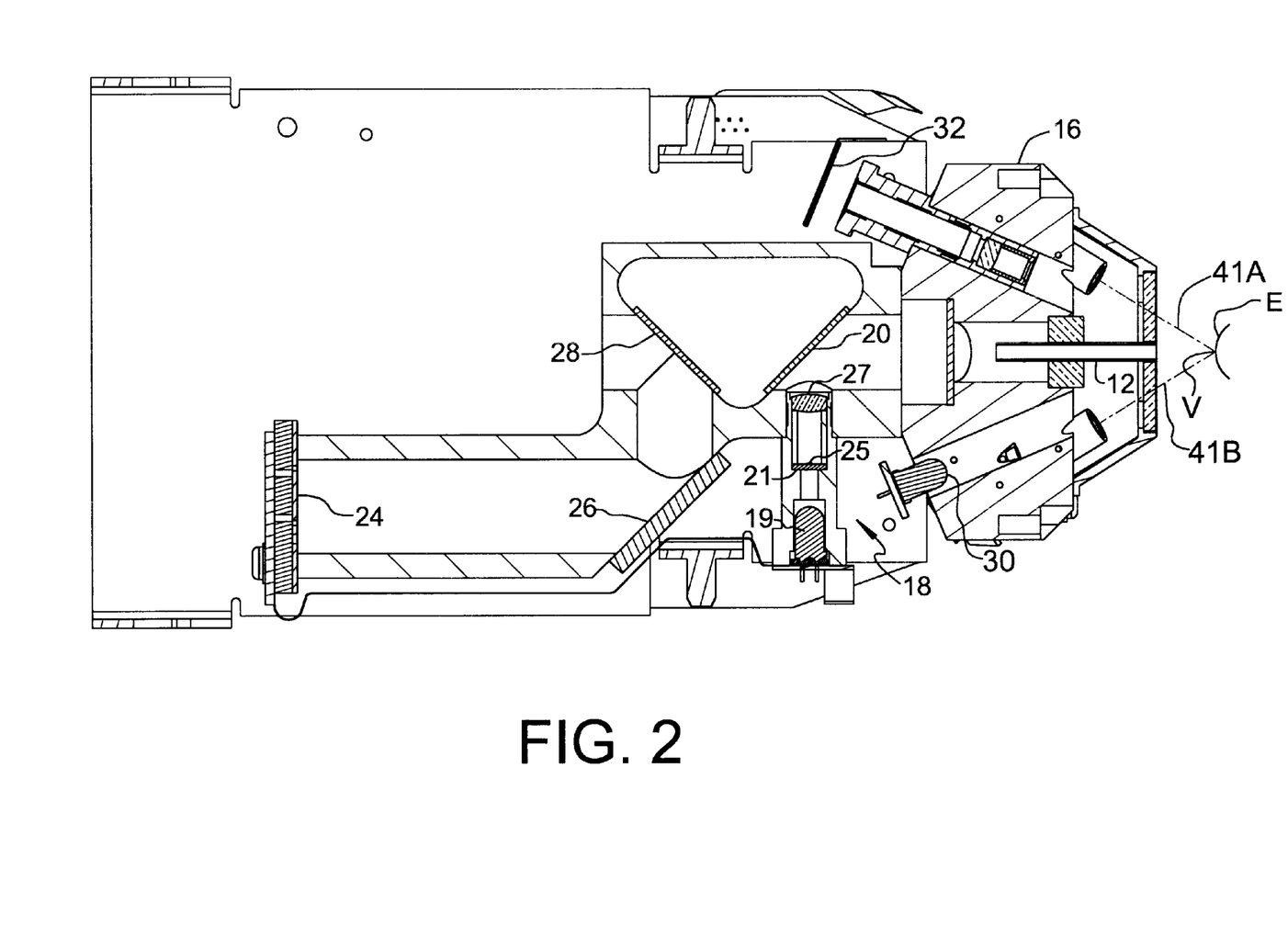
FIG. 2 is a sectional view of an optical block portion of the ophthalmic instrument shown in FIG. 1.

FIG. 2 shows a preferred fixation target projecting system 18 in greater detail. An LED 19 emits light that passes through a finely ground diffuser element 21 having a central target dot 25 painted translucent red. The light from diffuser element 21 then passes through a collimating lens 27 before the collimated target light is reflected by beamsplitter 20 to follow optical axis 14. The use of a relatively dark target dot against a bright background field is preferred because the bright background light helps to illuminate the patient's eye E to aid the operator's direct view of the eye along optical axis 14. Additional light sources (not shown) mounted in or near nosepiece 16 may be employed to help illuminate eye E.

Attention is directed now to the elements mounted in or on nosepiece 16. As mentioned above, instrument 10 is illustrated as being a non-contact tonometer, and thus it includes an applanation emitter 30 for obliquely illuminating the eye during discharge of the fluid pulse, and an applanation detector 32 arranged on an opposite side of the eye for receiving light reflected from the cornea and registering a peak signal at the moment the corneal surface is flattened ("applanated") by the fluid pulse. Those familiar with the non-contact tonometers will recognize that applanation emitter 30 and applanation detector 32 are parts of a well-known prior art arrangement for determining the moment applanation occurs based on reflected light from the corneal surface.

Also within nosepiece 16 are elements of a position detection system forming part of an alignment system according to an embodiment of the present invention. More specifically, the schematic representation of FIG. 1 shows light source 40A on one side of optical axis 14 and a detector 42A on an opposite side of optical axis 14 used for position detection. In actual practice, nosepiece 16 supports a second light source 40B and a second detector 42B, which can be seen in the view of FIG. 3. In the embodiment described at present, light sources 40A and 40B are located just below the horizontal plane containing optical axis 14, while detectors 42A and 42B are located just above the horizontal plane containing optical axis 14, thereby leaving space in the horizontal plane for applanation emitter 30 and applanation detector 32. First light source 40A directs a first beam of light along a first illumination axis 41A for illuminating eye E, and first detector 42A defines a first light-detecting area for receiving an image of first light source 40A formed by light reflected from the eye. Light traveling along first illumination axis 41A passes through a collector lens 44A and is obliquely incident to the generally spherical surface of the cornea, where it is reflected toward first detector 42A. A collector lens 46A in front of first detector 42A substantially collimates the divergent beam coming from the generally spherical surface of the cornea, whereby a spot of illumination is received on the light-detecting area defined by first detector 42A. Essentially, first detector 42A detects an apparent or virtual source behind the cornea. Second light source 40B, second illumination axis 41B, collector lenses 44B and 46B, and second detector 42B form a similar system, and are preferably arranged in opposing symmetry about the vertical plane containing optical axis 14. In a preferred construction, position light sources 40A and 40B and applanation emitter 30 are infrared light-emitting diodes for invisibility to the patient, and are mounted or formed on a single flexible circuit board to allow assembly of the instrument with greater ease. Similarly, first and second detectors 42A, 42B are preferably carried by a flexible circuit board for easy assembly.

Figure 3:
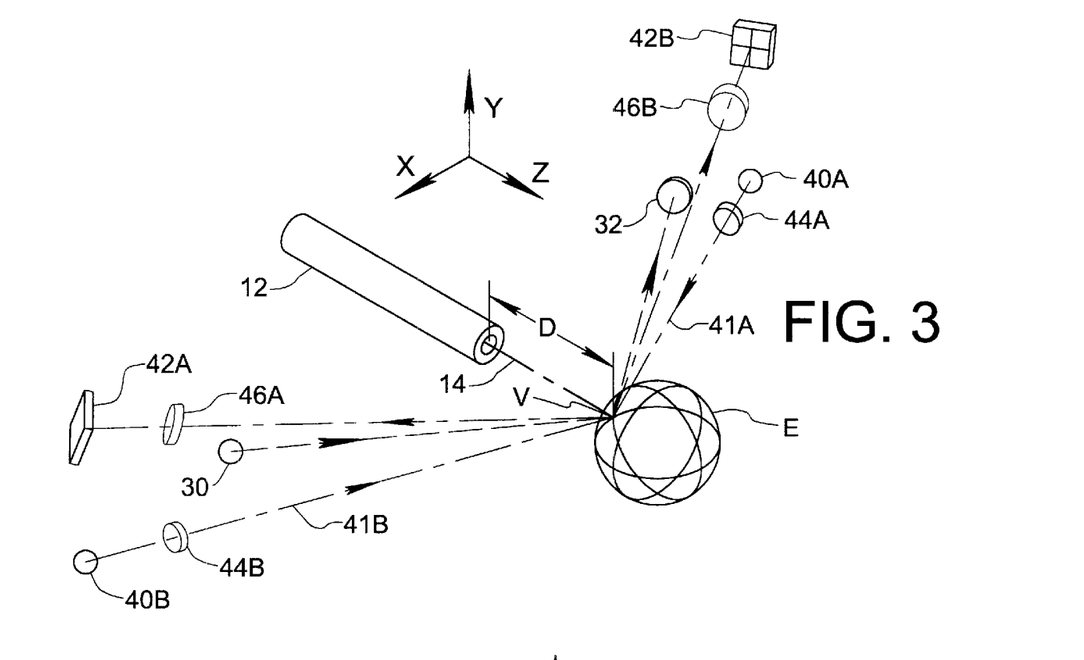
FIG. 3 is a schematic perspective view showing the arrangement of elements of a position detection system forming part of the alignment system in accordance with a preferred embodiment of the present invention.

In the illustration of FIG. 3, the instrument as represented by the exit end of fluid discharge tube 12 and the eye as represented by the corneal vertex V are shown in a state of three-dimensional (X-Y-Z) alignment. In the present embodiment, alignment is achieved when optical axis 14 intersects and is normal to corneal vertex V, and the exit end of fluid discharge tube 12 is a predetermined firing distance D away from corneal vertex V in a Z-axis direction. The orientation of first detector 42A and that of second detector 42B are chosen such that the central ray of the corresponding corneally reflected illumination beam is normal to the light-detecting area of the associated detector and arrives substantially at a central point of the light-detecting area when X-Y-Z alignment exists.

Figure 4:
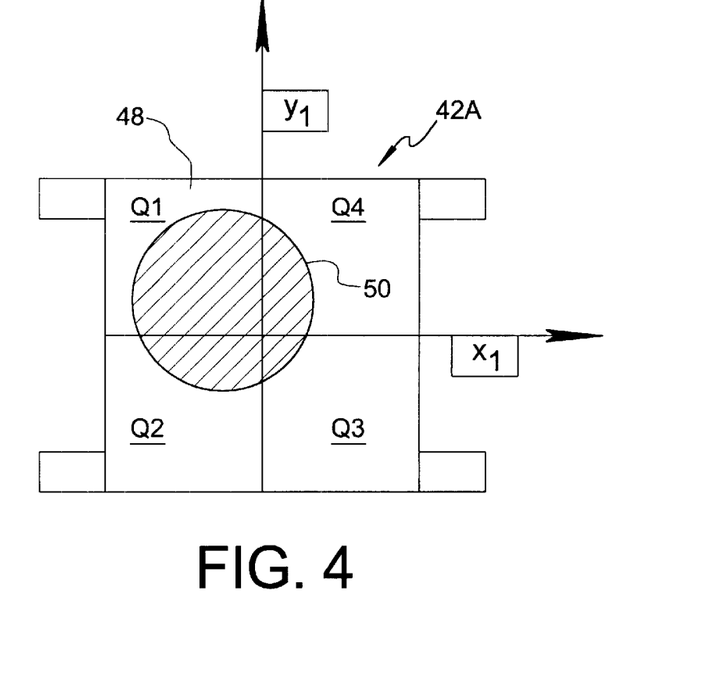
FIG. 4 is a detail view of a quad-cell detector of the position detection system shown in FIG. 2.

FIG. 4 shows a light-detecting area 48 of first detector 42A, with the understanding that the accompanying description also applies as well to second detector 42B. An image of light source 40A appears as a spot 50 on light detecting area 48. In the present embodiment, first detector 42A is a quad-cell detector comprising four quadrants Q1, Q2, Q3, and Q4 each providing a signal proportional to the illumination optical power received thereby. The size of each quadrant is preferably on the order of about 1.3 mm×1.3 mm, with a separation distance of about 0.1 mm between adjacent quadrant edges. The size of illumination spot 50 should be on the order of the size of one quadrant for meaningful x-y resolution. The size of illumination spot 50 will change during Z-axis adjustment as instrument 10 is moved closer to or further away from the eye. Moreover, the rate of change in spot size increases as the instrument moves closer to the eye. Therefore, it is desirable to optimize the system for a range of Z-axis positions centered about the predetermined firing distance D (i.e. +/−2.00 mm) such that the change in spot size for Z-axis positions throughout the range is minimized. Optimization can be carried out by selecting an appropriate front focal length for collector lenses 46A, 46B that causes the light striking detectors 42A, 42B to transition from being slightly convergent to being slightly divergent as the instrument is moved through the range of Z-axis positions toward the eye, wherein the light striking detectors 42A, 42B is approximately collimated when the instrument is at the predetermined firing distance D. In practice, it has been found that the firing distance D should be just beyond the front focal length of collector lenses 46A, 46B.

As will be understood, the signals from quadrants Q1–Q4 of first detector 42A are indicative of the local two-dimensional location $(x_1, y_1)$ of the centroid of spot image 50 in light detecting area 48, and the signals from quadrants Q1–Q4 of second detector 42B are indicative of the local two-dimensional location $(x_2, y_2)$ of a similar spot formed on the light detecting area of the second detector. The local x position is given by comparing the signal strengths from each quadrant as follows:

$$x=(Q3+Q4-Q1-Q2)/(Q1+Q2+Q3+Q4).$$

Likewise, the local y position is given by comparing the signal strengths from each quadrant as follows:

$$y=(Q1+Q4-Q2-Q3)/(Q1+Q2+Q3+Q4).$$

Figure 5:
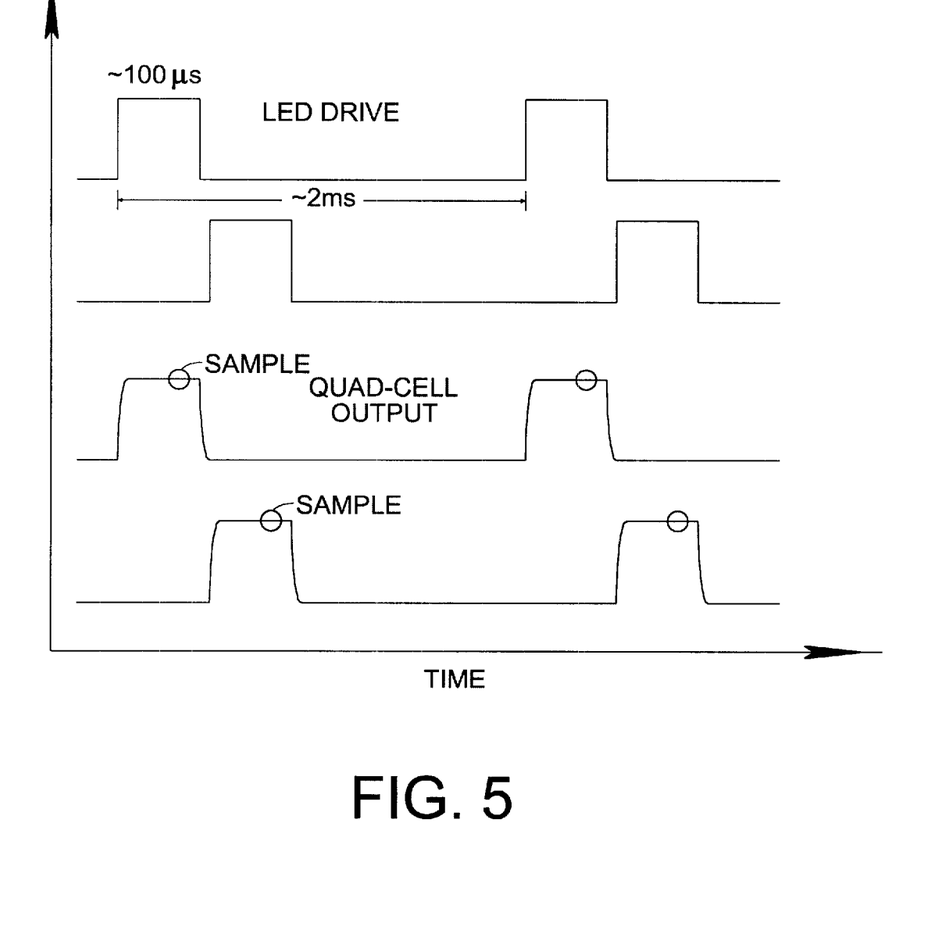
FIG. 5 is an electronic timing diagram relating to illumination and sampling of the quad-cell detector shown in FIG. 4.

In order to avoid interference, provide sufficient illumination intensity, and reduce power consumption, first light source 40A and second light source 40B are illuminated sequentially, and first detector 42A and second detector 42B are sampled sequentially. FIG. 5 is a timing diagram that illustrates that one light source is pulsed for a duration of about 100 μs and then sampled, and then the other light source is pulsed for the same duration and sampled. The cycle is repeated at approximately every 2 ms.

Figure 6:
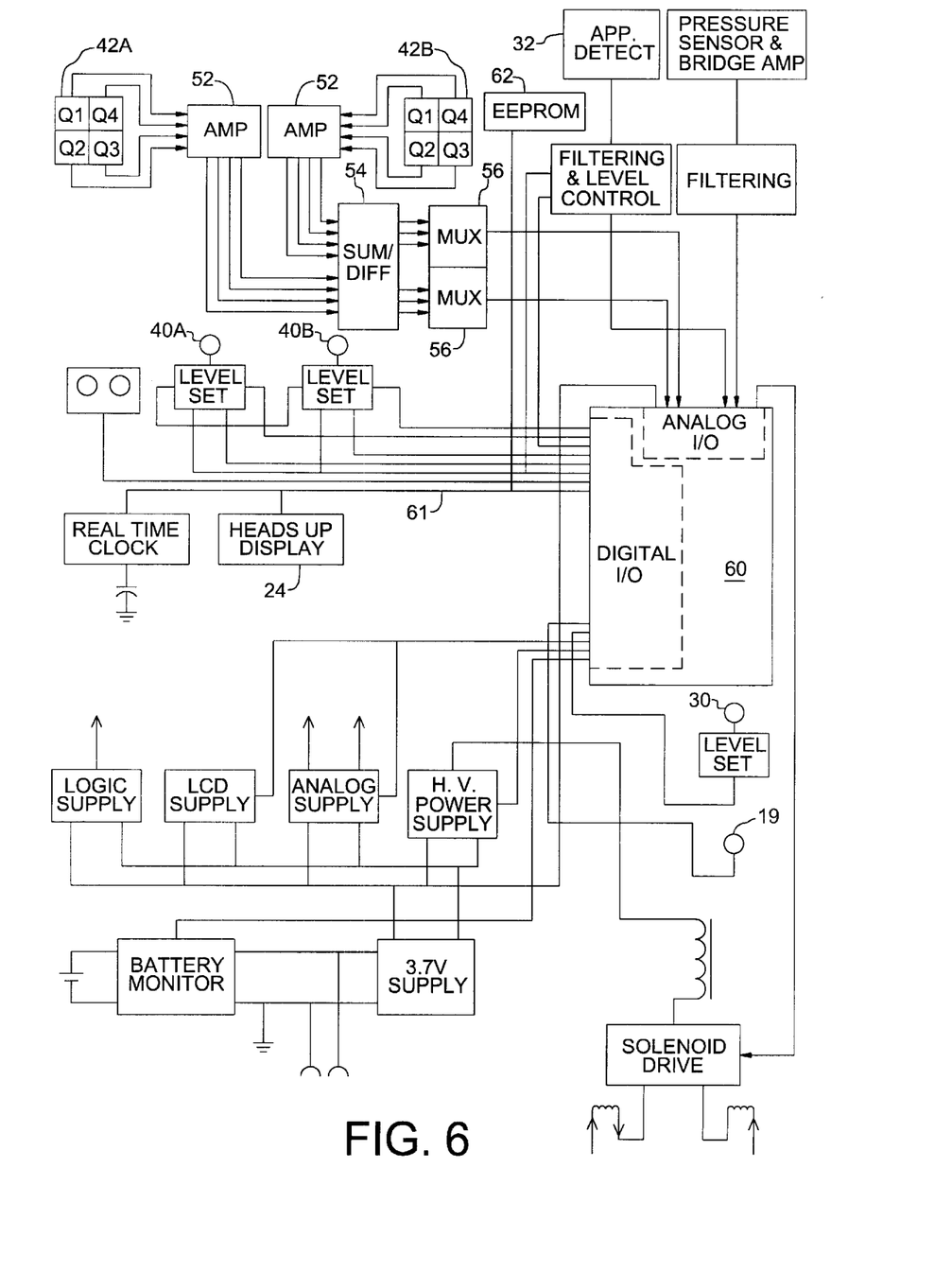
FIG. 6 is an electronic block diagram of the ophthalmic instrument shown in FIG. 1.

Referring also now to FIG. 6, the analog signals from quadrants Q1–Q4 of detectors 42A, 42B are fed to amplifiers 52 and then input to a sum/difference circuit 54. Sum/difference circuit 54 provides three outputs for each position detector 42A, 42B. Two of the outputs are the respective x and y numerators in the above equations, and the third output is the denominator common to both equations. The output signals are multiplexed by a multiplexor 56 and then provided as analog input to a microprocessor 60, which provides on-board analog-to-digital conversion of the signals. Microprocessor 60 is programmed to calculate the final spot locations $(x_1, y_1)$ and $(x_2, y_2)$.

While the present embodiment is described as employing quad-cell detectors, it is possible to substitute other detector types and configurations for purposes of the present invention. For example, a variety of position sensitive devices (PSDs) are commercially available that can provide local x-y signal information. Also, it is possible to arrange four discrete photosensitive detectors in a quadrant configuration to mimic the quad-cell detector described above.

The global X-Y-Z alignment status of ophthalmic instrument 10 relative to the eye is then computed by inputting coordinates $x_1, y_1$ from first detector 42A and coordinates $x_2, y_2$ from second detector 42B to a plurality of predetermined geometric relationships stored in memory 62 during calibration of instrument 10. More specifically, geometrical relationships giving the global position coordinates X, Y, and Z can be determined by multiple regression as follows:

$$X=R_1x_1+R_2y_1+R_3x_2+R_4y_2+R_5,$$

$$Y=R_6x_1+R_7y_1+R_8x_2+R_9y_2+R_{10}, \text{ and}$$

$$Z=R_{11}x_1+R_{12}y_1+R_{13}x_2+R_{14}y_2+R_{15},$$

wherein the regression coefficients $R_1$–$R_{15}$ are found during instrument calibration measurements using an artificial eye.

Figure 7:
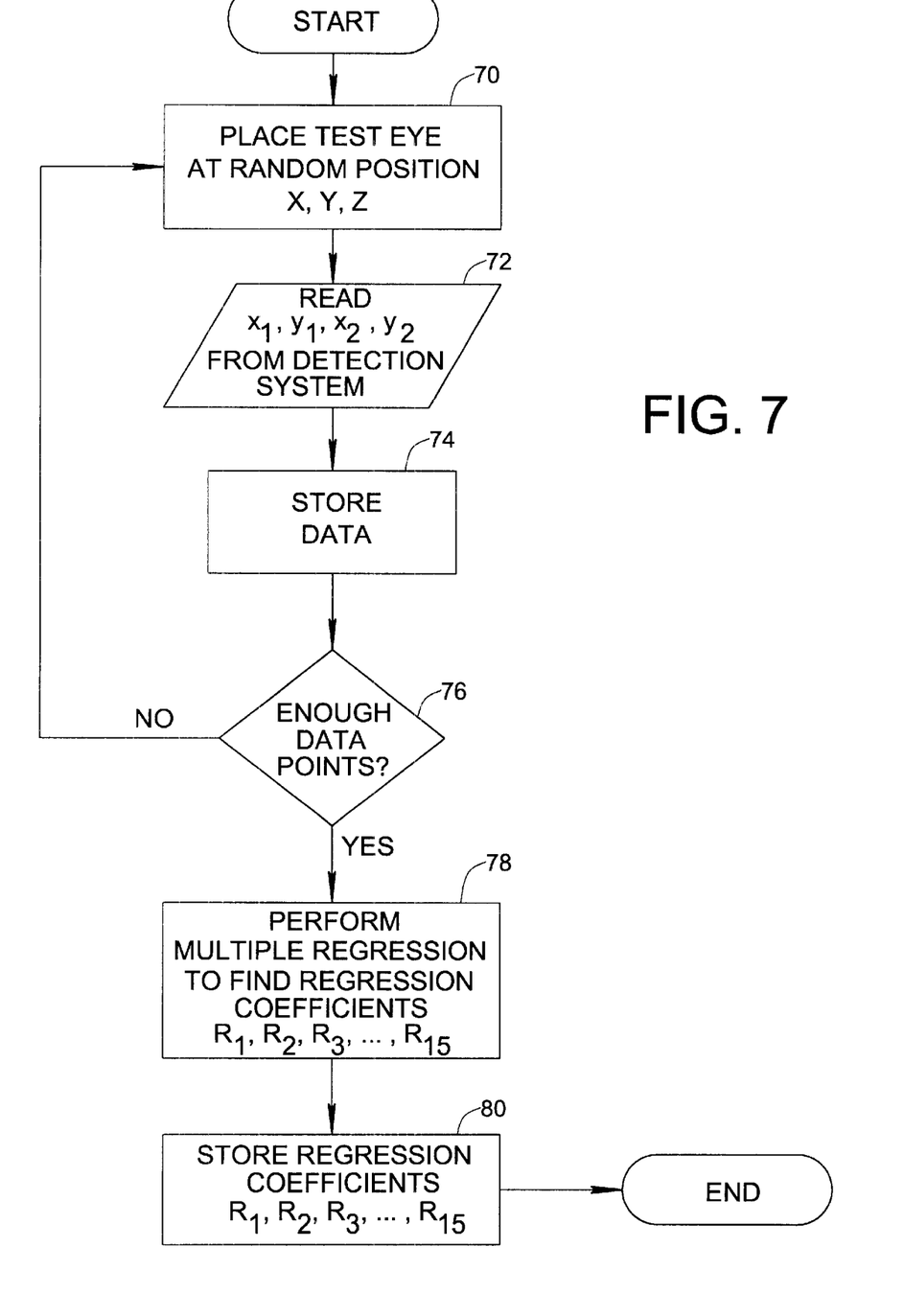
FIG. 7 is a flow diagram of steps followed to calibrate the position detection system shown in FIG. 2.

FIG. 7 is a flow diagram showing the steps followed to calibrate the position detection system of the present invention. First, according to step 70, an artificial "test" eye is placed at a random, known position X, Y, Z relative to instrument 10. Then, as indicated by steps 72 and 74, the local spot positions $(x_1, y_1)$ and $(x_2, y_2)$ are read from the position detection system and stored in a table with the corresponding known global coordinates X, Y, Z. If a sufficient number of data points have been measured according to query 76, multiple regression is performed in step 78 to find the regression coefficients $R_1$–$R_{15}$, which are then stored in memory pursuant to step 80. If more data points are needed according to query 76, the process returns to step 70 and is repeated. It is preferable to calibrate the position detection system using a large number random locations of the artificial eye, as this will provide greater accuracy in the determination of the regression coefficients, and ultimately provide improved accuracy in the computed X, Y, Z location of a patient's eye.

Primarily because the position detection system of the present invention obviates the need for scanning a CCD array having a large number of pixels, it provides X-Y-Z alignment status information at a much higher repetition rate than systems of the prior art. As noted above, a faster system is particularly useful for alignment of handheld instruments, which may be actuated to take a measurement as soon as X-Y-Z alignment is confirmed. Thus, the system reduces the lag time between confirmation of alignment and measurement during which further relative movement between the instrument and eye can occur. Moreover, the position detection system of the present invention can be calibrated periodically by manufacturer personnel to ensure alignment accuracy.

Figure 8:
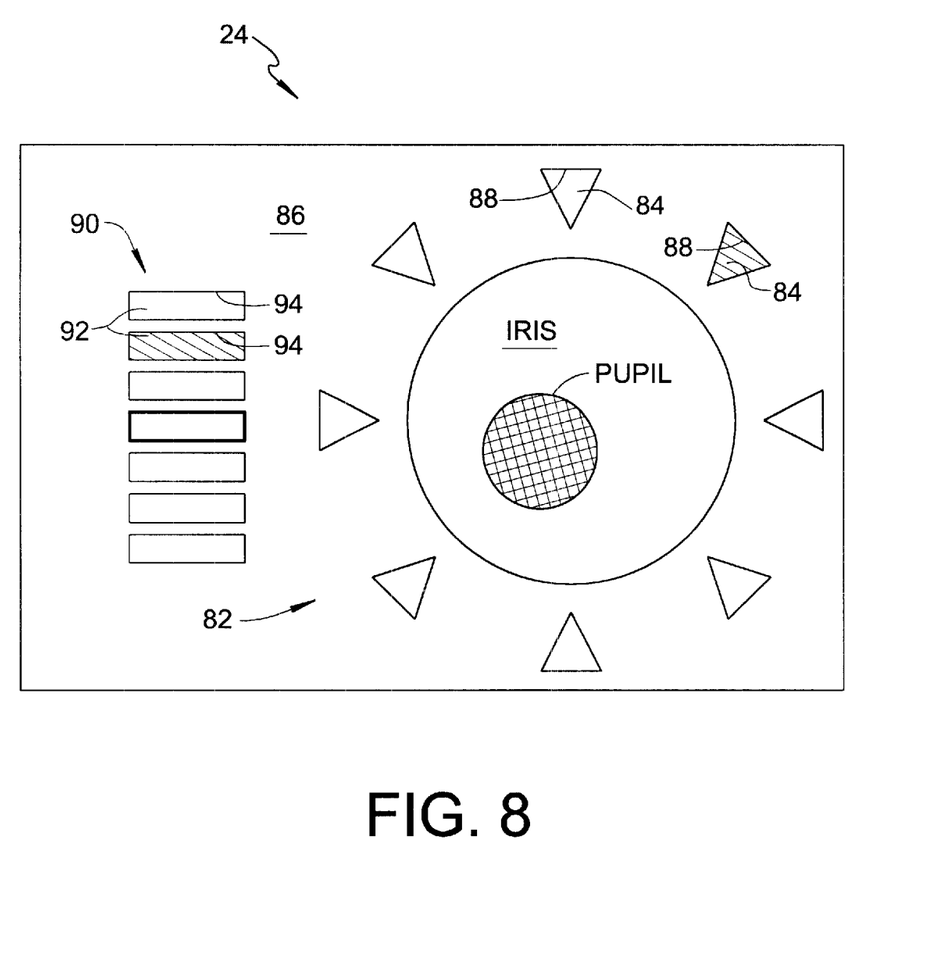
FIG. 8 is an enlarged view of a "heads up" display forming part of the alignment system in accordance with a preferred embodiment of the present invention for providing alignment instructions to an operator for aligning the instrument relative to an eye to be tested.

FIG. 8 shows an enlarged view of "heads-up" display 24 of instrument 10 as it appears to an operator viewing through eyepiece 22 along optical axis 14. Display 24 assists the operator in aligning the instrument by presenting the computed X-Y-Z alignment status in a format that instructs the operator regarding movement of the instrument necessary to achieve alignment. Heads-up display 24 comprises a polar array 82 of light-emitting diodes 84 masked by an overlay 86 having light-transmitting directional pointers 88 for providing an X-Y alignment instruction to the operator. The LEDs 84 in polar array 82 are each connected to microprocessor 60 by way of an $I^2C$ line 61 and a serial-to-parallel converter (not shown), whereby the LEDs are selectively illuminated depending upon the X-Y alignment status of the instrument relative to the eye. In particular, an LED 84 is illuminated corresponding to an appropriate directional pointer instructing the operator of the direction to move the instrument to align optical axis 14 with corneal vertex V. When X-Y alignment is achieved, all the LEDs 84 in polar array 82 can be illuminated in continuous or pulsing fashion to communicate a condition of X-Y alignment to the operator. Heads-up display 24 further comprises a linear array 90 of light-emitting diodes 92 positioned to correspond with light-transmitting rectangles 94 in overlay 86 for purposes of Z-axis alignment. The LEDs 92 in linear array 90 are each connected to microprocessor 60 by way of $I^2C$ line 61 and a serial-to-parallel converter (not shown), whereby the LEDs are selectively illuminated depending upon the Z alignment status of the instrument relative to the eye. More specifically, and by way of non-limiting example, the top and bottom LEDs in linear array 90 are the same color (i.e. red), the middle LED is another color (i.e. green), and the LEDs between the top Led and middle LED and between the bottom LED and the middle LED are all yet another color (i.e. yellow). When the instrument is too close to the eye, both red LEDs flash as a warning to the operator. The lower red and yellow LEDs indicate the instrument should be moved away from the eye, while the upper red and yellow LEDs indicate the instrument should be moved toward the eye. The green LED indicates that Z-axis alignment is reached. Currently, it is preferred to provide LEDs 84 and 92 on a single circuit board, and to use photographic film to form overlay 86, which may be separated from the LED circuit board by a spacer (not shown).

As can be seen in FIG. 1, the actual heads-up display 24 is located in the instrument at a location off of optical axis 14. An image of heads-up display 24 is presented to the operator along optical axis 14 by means of mirror 26 and beamsplitter 28. The X-Y polar array 82 is arranged circumferentially about a macro image of the patient's eye through macro-lens 23, whereby the operator can see the pupil and surrounding iris along with superimposed instructional display cues provided by heads-up display 24. For example, in FIG. 8, the operator is being instructed to move the instrument lower and to the left for X-Y alignment, and closer to the eye for Z alignment.

What is claimed is:

1. An alignment system for assisting an operator in aligning an ophthalmic instrument relative to an eye of a patient, said alignment system comprising:

a measurement axis;

means for projecting a visible fixation target image along said measurement axis for viewing by said patient;

an optical axis along which said operator directly views said eye;

opto-electronic position detection means for providing signal information regarding the alignment status of said ophthalmic instrument relative to said eye; and a display connected to said opto-electronic position detection means for guiding said operator in achieving alignment of said ophthalmic instrument relative to said eye based on said signal information.

2. The alignment system according to claim 1, wherein said optical axis is coincident with said measurement axis.

3. The alignment system according to claim 1, wherein said ophthalmic instrument is a non-contact tonometer comprising a fluid discharge tube having a fluid passage in axial alignment with said measurement axis for directing a fluid pulse along said measurement axis toward said eye, and said fixation target image is projected through said fluid passage of said fluid discharge tube.

4. The alignment system according to claim 3, wherein said fixation target image is surrounded by a bright field for illuminating said eye to aid said operator in directly viewing said eye.

5. The alignment system according to claim 1, further comprising means for projecting an image of said display to said operator along said optical axis, whereby said image of said display is superimposed with a real image of said eye.

6. The alignment system according to claim 5, wherein said display includes a polar array of light emitting diodes for providing an X-Y alignment instruction, and said polar array surrounds said real image of said eye when said image of said display is superimposed with said real image of said eye.

7. The alignment system according to claim 5, wherein said means for projecting said visible fixation target image includes a first beamsplitter arranged on said optical axis and said means for projecting an image of said display includes a second beamsplitter arranged on said optical axis.

8. The alignment system according to claim 7, wherein beam displacement caused by said first beamsplitter is compensated by an opposite beam displacement caused by said second beamsplitter for light transmitted along said optical axis.

9. The alignment system according to claim 1, wherein said opto-electronic position detection means includes a first light source for illuminating said eye with a first beam of light along a first illumination axis, a second light source for illuminating said eye with a second beam of light along a second illumination axis different from said first illumination axis, a first quad-cell detector defining a first light-detecting area for receiving an image of said first light source, and a second quad-cell detector defining a second light-detecting area for receiving an image of said second light source.

10. In an ophthalmic instrument for enabling an operator to measure a parameter of an eye of a patient, said ophthalmic instrument having a measurement axis for alignment normal to a corneal pole of said eye and means for projecting a visible fixation target image along said measurement axis for viewing by said patient, the improvement comprising:

an optical axis along which said operator directly views said eye;

wherein said fixation target image is surrounded by a bright field for illuminating said eye to aid said operator in directly viewing said eye.

11. The improvement according to claim 10, wherein said optical axis is coincident with said measurement axis.

12. The improvement according to claim 10, wherein said ophthalmic instrument is a non-contact tonometer comprising a fluid discharge tube having a fluid passage in axial alignment with said measurement axis for directing a fluid pulse along said measurement axis toward said eye, and said fixation target image is projected through said fluid passage of said fluid discharge tube.

* * * * *